US010925994B2

(12) United States Patent
Cullen et al.

(10) Patent No.: US 10,925,994 B2
(45) Date of Patent: Feb. 23, 2021

(54) COMPOSITION

(71) Applicant: SYSTAGENIX WOUND MANAGEMENT IP CO. BV., Amsterdam (NL)

(72) Inventors: Breda Mary Cullen, Skipton (GB); Alexander Waite, North Yorkshire (GB); Derek Silcock, Skipton (GB)

(73) Assignee: SYSTAGENIX WOUND MANAGEMENT, LIMITED, West Sussex (GB)

( * ) Notice: Subject to any disclaimer, the term of this patent is extended or adjusted under 35 U.S.C. 154(b) by 165 days.

(21) Appl. No.: 15/576,139

(22) PCT Filed: May 26, 2016

(86) PCT No.: PCT/EP2016/061959
§ 371 (c)(1),
(2) Date: Nov. 21, 2017

(87) PCT Pub. No.: WO2016/189113
PCT Pub. Date: Dec. 1, 2016

(65) Prior Publication Data
US 2018/0133358 A1 May 17, 2018

(30) Foreign Application Priority Data
May 27, 2015 (GB) ..................... 1509044

(51) Int. Cl.
A61L 15/42 (2006.01)
A61L 15/26 (2006.01)
A61L 15/38 (2006.01)

(52) U.S. Cl.
CPC ............. A61L 15/425 (2013.01); A61L 15/26 (2013.01); A61L 15/38 (2013.01)

(58) Field of Classification Search
CPC ......... A61L 15/425; A61L 15/26; A61L 15/38
USPC ...................................... 424/94.1
See application file for complete search history.

(56) References Cited

U.S. PATENT DOCUMENTS

| 1,355,846 | A | 10/1920 | Rannells |
|---|---|---|---|
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |

(Continued)

FOREIGN PATENT DOCUMENTS

| AU | 550575 B2 | 3/1986 |
|---|---|---|
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

(Continued)

Primary Examiner — Jennifer M. H. Tichy
(74) Attorney, Agent, or Firm — Foley & Lardner LLP

(57) ABSTRACT

A polyurethane foam wound dressing, the foam integrally comprising an oxidoreductase enzyme and a substrate for the enzyme. The foam is produced by mixing a polyurethane polymer, water, an oxidoreductase enzyme and substrate for the enzyme and drying the resulting product.

9 Claims, 2 Drawing Sheets

(56) References Cited

U.S. PATENT DOCUMENTS

Figure 1:
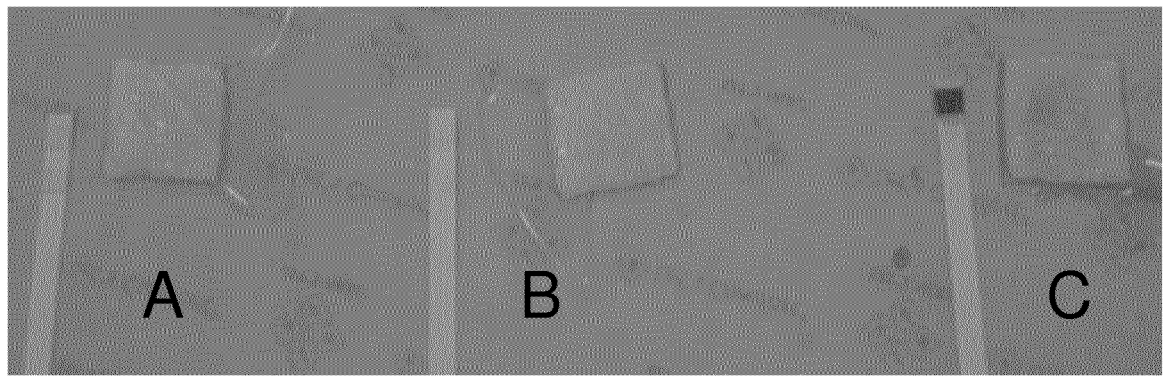

| | | |
|---|---|---|
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,326,410 B1 * | 12/2001 | Cheong .................. A61L 15/225 521/117 |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2012/0269879 A1 * | 10/2012 | Watson .................. A61L 15/60 424/445 |
| 2013/0336899 A1 * | 12/2013 | Li ........................ A61K 31/722 424/10.3 |
| 2014/0023597 A1 | 1/2014 | Barrett et al. |
| 2014/0154193 A1 | 6/2014 | Barrett et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 541391 A1 | 5/1993 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2403146 A | 12/2004 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2008/049578 A2 | 5/2008 |
| WO | 2013/188497 A2 | 12/2013 |

OTHER PUBLICATIONS

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

(56) References Cited

OTHER PUBLICATIONS

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report & Written Opinion in International Application No. PCT/EP2016/061959, dated Dec. 1, 2016 (12 pages).

* cited by examiner

COMPOSITION

The present invention relates to a wound dressing with antimicrobial activity and wound healing properties.

Infected wounds generally produce substantially more exudate than uninfected wounds. There is an ongoing requirement for improved wound dressings that address both the infection and the exudate. Although a range of antimicrobial products are commercially available, these are for the most part cytotoxic owing to the non-discriminatory mode of action whereby host cells are disrupted along with bacterial cells.

It is an object of the invention to provide an improved wound dressing for treating wounds.

In one aspect, a polyurethane foam wound dressing is disclosed, the foam integrally comprising an oxidoreductase enzyme and a substrate for the enzyme.

The foam can be a "hydropolymer" meaning that it is a water-swellable polymer. The foam serves to absorb wound exudate to avoid maceration whilst swelling to conform to the wound bed. In addition, exudates are retained so that moisture levels within the wound are maintained to prevent drying out of the wound bed.

In one embodiment, the enzyme and substrate are added during production of the foam, and are therefore integrated in the foam. This means the enzyme and substrate are constituent components of the foam. One of the advantages of the invention wound dressing is that this integration means the enzyme and substrate are retained within the structure of the foam, rather than being easily washed out by wound exudate as happens when the components are not integrated during manufacture. Consequently the wound dressing is able to provide sustained hydrogen peroxide production under highly exudative wound conditions.

In use, when the foam is hydrated, for example, by wound exudate, the integral enzyme is able to metabolise the integral enzyme substrate producing hydrogen peroxide. For example, glucose oxidase metabolises glucose producing hydrogen peroxide.

Preferably, hydrogen peroxide is generated at levels of over 50 mg/l including over 100 mg/l, 200 mg/l, 300 mg/l, 500 mg/l or 1000 mg/l.

Hydrogen peroxide plays multiple roles in wound healing, both in terms of microbial defence and stimulation of healing. During wound healing hydrogen peroxide is released by inflammatory cells as part of the immune response. Low levels of hydrogen peroxide are also known to modulate several key processes including; cell migration, proliferation and angiogenesis. The wound dressing provides an exogenous source of hydrogen peroxide that can mimic the body's own immune response. Hydrogen peroxide is also a broad spectrum antimicrobial which disrupts bacterial cells and processes key to growth and survival. In this context hydrogen peroxide disrupts the outer membrane of the bacteria and processes key to tissue invasion.

In a preferred embodiment, the oxidoreductase enzyme is glucose oxidase and the substrate is glucose. The glucose substrate can be in the form of honey.

In a further preferred embodiment, the oxidoreductase enzyme is fructose oxidase and the substrate is fructose. In a further preferred embodiment, the oxidoreductase enzyme is hexose oxidase and the substrate is a hexose sugar. In a further preferred embodiment, the oxidoreductase enzyme is cholesterol oxidase and the substrate is cholesterol. In a further preferred embodiment, the oxidoreductase enzyme is galactose oxidase and the substrate is galactose. In a further preferred embodiment, the oxidoreductase enzyme is pyranose oxidase and the substrate is pyranose. In a further preferred embodiment, the oxidoreductase enzyme is choline oxidase and the substrate is choline. In a further preferred embodiment, the oxidoreductase enzyme is pyruvate oxidase and the substrate is pyruvate. In a further preferred embodiment, the oxidoreductase enzyme is glycollate oxidase and the substrate is glycollate.

A mixture of oxidoreductase enzymes and their corresponding substrates can also be used. For example, glucose oxidase, glucose, fructose oxidase and fructose can be used.

The enzyme can be present in the foam at a concentration of at least 0.01 mg enzyme per gram of foam, for example, 0.01 mg to 1 mg or 0.1 mg to 1 mg enzyme per gram of foam.

The substrate can be added at a concentration of at least 1% (w/w), including 1-20% (w/w) or at least 5% (w/w), for example 5-20% (w/w).

The foam wound dressing can have a density of at least 0.28 g/cm$^3$, or at least 0.30 g/cm$^3$, preferably from 0.28 to 0.5 g/cm$^3$, including from 0.32 to 0.48 g/cm$^3$, containing 0.01 to 1 mg enzyme per gram of foam and 1 to 20% (w/w) of substrate.

The foam preferably has an elongation at break of at least 150%, preferably at least 300%, preferably from 500% to 1000%. The foam is hydrophilic and absorbs aqueous fluids such as wound exudate with swelling.

The foam can be highly cross-linked.

The foam can be substantially insoluble in water.

Preferably, the foam has an absorbency of at least 3 g saline/g, preferably at least 5 g/g, preferably from 8 to 20 g/g.

Preferably, the foam has a swellability in water (degree of swelling on complete saturation with an aqueous medium) of at least 50%, at least 100% or at least 200%, including 400-800% (expressed in terms of the increase in volume).

The foam can contain less than 1% by weight of water-soluble alcohols.

The foam can be as described in EP-A-0541391 or EP-A-0541390, the entire contents of which is incorporated herein by reference. An example of the foam is available under the trade mark Tielle™, manufactured by Systagenix.

The foam can have an open-celled morphology. The cells can be regular in size and shape, with smooth edges to the pores in the walls of the cells. Typically, the cells of the foams have an average diameter in the range of 0.1 to 0.6 mm.

The foam can be obtained or is obtainable by mixing a polyurethane prepolymer, water, an oxidoreductase enzyme and a substrate for the enzyme, and then drying the product.

In a preferred embodiment, a monohydric alcohol is added when making the foam. Alternatively, a dihydric or polyhydric alcohol, such as ethylene glycol or glycerol, can be added.

In a further preferred embodiment, a rubber is added when making the foam. The rubber can be natural or synthetic, for example, acrylic rubber.

In a preferred embodiment, a monohydric alcohol and a rubber are added when making the foam.

Thus, the foam can be made by mixing a polyurethane prepolymer, a monohydric alcohol, water, a rubber, an oxidoreductase enzyme and a substrate for the enzyme, and then drying the product.

The prepolymer used for manufacturing the foam is preferably hydrophilic, preferably an isocyanate-capped polymer, such as an ethyleneoxy/propyleneoxy copolymer. For example, one of the prepolymers is available under the trade Mark HYPOL™ from Dow Chemical Company. The prepolymer can have from 0.5 to 4.8 meq NCO groups/g, preferably 0.5 to 1.2 meq NCO groups/g or 0.5 to less than 1.2 meq NCO groups/g.

The prepolymer can be added in a quantity of 1 part by weight.

0.4 to 1.0 parts including 0.5 to 1.0 and 0.6 to 0.9 parts by weight of water can be added. The water can be added in the presence of from 0.05 to 0.4 parts by weight of a monohydric alcohol including 0.05 to 0.25, including 0.1 to 0.25, parts by weight of methanol or from 0.1 to 0.3 parts by weight of ethanol.

The alcohol used to produce the foam can be methanol, ethanol or propanol, preferably methanol.

Once the components are mixed, the product can be dried such that the amount of water-soluble alcohol remaining in the product is less than 1% by weight, including less than 0.1%.

The rubber included in the foam may be either natural or synthetic and/or can be included in a proportion of up to 30% by weight of the wet composition or from 0.03 to 0.3, including 0.05 to 0.2, parts by weight of rubber, including 0.05 to 0.15 parts by weight.

The rubber can be added in the form of a latex, i.e. a suspension or emulsion of the rubber in an aqueous medium. The latex will generally comprise 40 to 70% solids by weight, e.g. 50 to 60% by weight.

Acrylic-based rubbers are preferred, such as an aqueous acrylic polymer emulsion. For example, rubber manufactured under the name PRIMAL™ by The Dow Chemical Company.

Other components may be added to the reaction mixture in the method, in order to give desired properties to the product.

For example, additional antimicrobial components (such as iodine, PHMB, chlorhexidine, silver, copper, surfactants), active components that promote healing (such as oxidised regenerated cellulose, antioxidants or anti-inflammatories) or biopolymers (such as alginates, carboxymethyl cellulose, chitosan, gelatin, collagen, hyaluronic acid).

For example, in addition to the monohydric alcohol, other alcohols, particularly polyols, may be included in the reaction mixture. For example, a polyol sold by Bayer AG under the trade mark Levagel™ may be used. After drying, the foams preferably contain less than 1% by weight of water soluble alcohols, and preferably less than 0.1% by weight. It is preferred that the foams are essentially free of water soluble alcohols (e.g. less than 0.01% by weight).

After mixing the prepolymer, water, oxidoreductase enzyme, substrate for the enzyme, and optionally the monohydric alcohol and rubber, the resulting product is dried. The drying can be carried out in an oven. Preferably, the drying can be carried out at between 50° C. and 80° C. The drying can be carried out at over 50° C., between 50° C. and 100° C., over 60° C., between 60° C. and 100° C. and over 70° C., between 70° C. and 100° C. A preferred temperature is between 60° C. and 70° C., including 65° C.

The drying can be carried out for at least 5 minutes, preferably at least 10 minutes including at least 20 minutes.

Prior to the drying step, a curing step can be carried out. The curing step can be conducted for at least 2, 5 or 10 minutes at ambient temperature, which can be approximately 20° C. to 25° C.

The polyurethane foam wound dressing can comprise glucose oxidase and glucose as constituent components, the foam produced by mixing an isocyanate-capped prepolymer, methanol, water, rubber, glucose oxidase and glucose and drying the mixture.

The wound dressing includes a polyurethane foam wound dressing with a density of at least 0.28 g/cm$^3$, the foam integrally comprising 0.1 mg to 1 mg oxidoreductase enzyme per gram of foam and 5-20% (w/w) substrate for the enzyme. The foam can be obtained or can be obtainable by mixing an isocyanate-capped polymer having 0.5 to 4.8 meq NCO groups/g in a quantity of 1 part by weight with 0.4 to 1.0 parts by weight of water, 0.05 to 0.4 parts by weight of monohydric alcohol and 0.03 to 0.3 parts by weight of rubber with the enzyme and substrate and drying the resulting product at over 50° C. and below 80° C. for at least 5 minutes.

The foam may be a reticulated, open-cell polyurethane or polyether foam that allows good permeability of wound fluids. One such foam material that has been used is the V.A.C.® Granufoam™ Dressing available from Kinetic Concepts, Inc. (KCI) of San Antonio, Tex. The reticulated pores of the Granufoam™ Dressing material are in the range of about 400 to 600 microns. A material with a higher, or lower, density (smaller pore size) than Granufoam® Dressing material may be desirable in some situations.

The foam material might also be a combination or layering of materials; for example, a first layer of hydrophilic foam might be disposed adjacent to a second layer of hydrophobic foam to form the foam. The foam may also be a reticulated foam that is later felted to a thickness of less about half its original thickness.

The foam can be used in any wound dressing requiring an absorbent layer and can be in conjunction with a secondary wound dressing or as a constituent part of a dressing.

The foam is generally the wound contacting layer. The dressings according may have a further layer between the wound contacting sheet as herein defined and the wound surface. For example, there may be a further layer or gel, or a wound contacting hydrogel net to assist removal of the wound dressing from the wound surface and to provide a more wound-friendly contacting surface.

The wound dressings can further comprise a backing layer located on the side of the absorbent layer opposite to the wound contacting layer. The backing layer is substantially liquid-impermeable to prevent leakage of wound exudate from the absorbent layer. For example, the backing layer may be formed from water vapour and gas-permeable, water and microbe-impermeable polyurethane film of the kind conventionally used for adhesive wound dressings. The backing layer can be bonded to the absorbent layer by heat or adhesive. A layer of medical grade pressure-sensitive adhesive can extend over the whole inner surface of the backing layer to bond the backing layer to the polyurethane foam. The adhesive also modifies the air- and water-permeability of the backing layer to give it the desired characteristics.

The backing layer can extend beyond the edges of the polyurethane foam to form a margin, and adhesive is provided on the margin for securing the margin of the backing layer to the skin of the patient around a wound. The same layer of adhesive can extend over the whole inner surface of the backing layer, for the reasons given above.

The foam can include topical medicaments and antiseptics, such as silver sulphadiazine, povidone iodine, chlorhexidine acetate and chlorhexidine gluconate, as well as other therapeutically useful additives such as polypeptide growth factors and enzymes.

The wound dressing can be as described in EP-A-0875222, WO00/56256 and WO02/026180, the entire contents of which is incorporated herein by reference, with the polyurethane foam described herein being used as the absorbent layer.

The wound dressings will be packaged in sterile packaging, and sterilized using routine methods, such as by gamma-irradiation.

The wound dressing can be used in a wide range of wound types. The wound can be uninfected, in which case the wound dressing prevents infection. Alternatively, the wound can be infected and the wound dressing treats or reduces the infection. The wound dressing can also be used for treating a range of microbial infections, including bacterial and fungal infections. The bacterial infections can be caused by a gram negative bacteria species or a gram positive bacteria species. The bacteria can be selected from the group consisting of *Pseudomonas, Streptococci, Salmonella,* Staphylococci, Enterococci, *Klebsiella, Bacillus, Clostridium, Campylobacter, Capnocytophaga, Escherichia, Proteus, Shigella, Bacteroides, Prevotella, Fusobacterium, Aeromonas* and *Acinetobacter*. The fungal infections can be caused by *Trichophyton, Aspergillus* or *Candida*.

A further aspect relates to a method of producing the polyurethane foam wound dressing comprising mixing
- a polyurethane prepolymer,
- water,
- an oxidoreductase enzyme and
- a substrate for the enzyme;
- and then drying the product.

In a preferred embodiment, a monohydric alcohol is added when producing the foam.

In a further preferred embodiment, a rubber is added when producing the foam.

In a preferred embodiment, a monohydric alcohol and a rubber are added when producing the foam.

Thus, in an embodiment, a method of producing the polyurethane foam wound dressing comprises mixing
- a polyurethane prepolymer,
- a monohydric alcohol,
- water,
- a rubber,
- an oxidoreductase enzyme and
- a substrate for the enzyme;
- and then drying the product.

The wound dressing can be obtained or obtainable according to a method described herein.

A further aspect relates to the polyurethane foam wound dressing defined herein for use in treating a wound, including an infected wound.

A yet further aspect relates to a method of treating a wound comprising applying the polyurethane foam wound dressing defined herein to a wound site.

Features of the second and subsequent aspects can be as for the first aspect mutatis mutandis.

FIGURES

The wound dressing will now be further described by way of reference to the following Examples and Figures which are provided for the purposes of illustration only and are not to be construed as being limiting. Reference is made to a number of Figures in which:

FIG. 1: Three foam samples; A. Polyurethane foam only, B. Polyurethane foam with honey, C. Polyurethane foam with honey and glucose oxidase. Only sample (C) containing both enzyme and substrate elicited a colour change in the hydrogen peroxide test strips. The other samples did not elicit a colour change.

Figure 2:
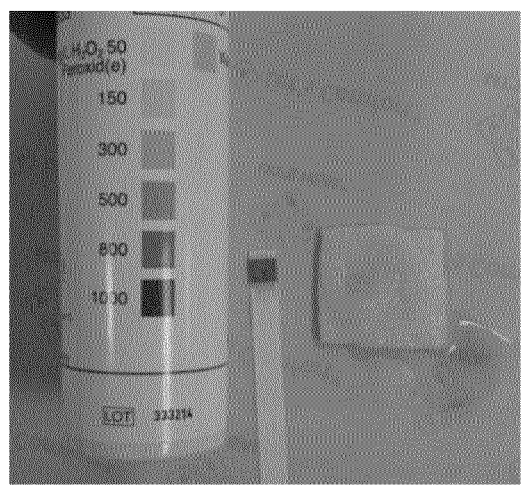

FIG. 2: The colour change elicited by Sample (C) indicated hydrogen peroxide levels generated to be approximately 1000 mg/l.

Figure 3:
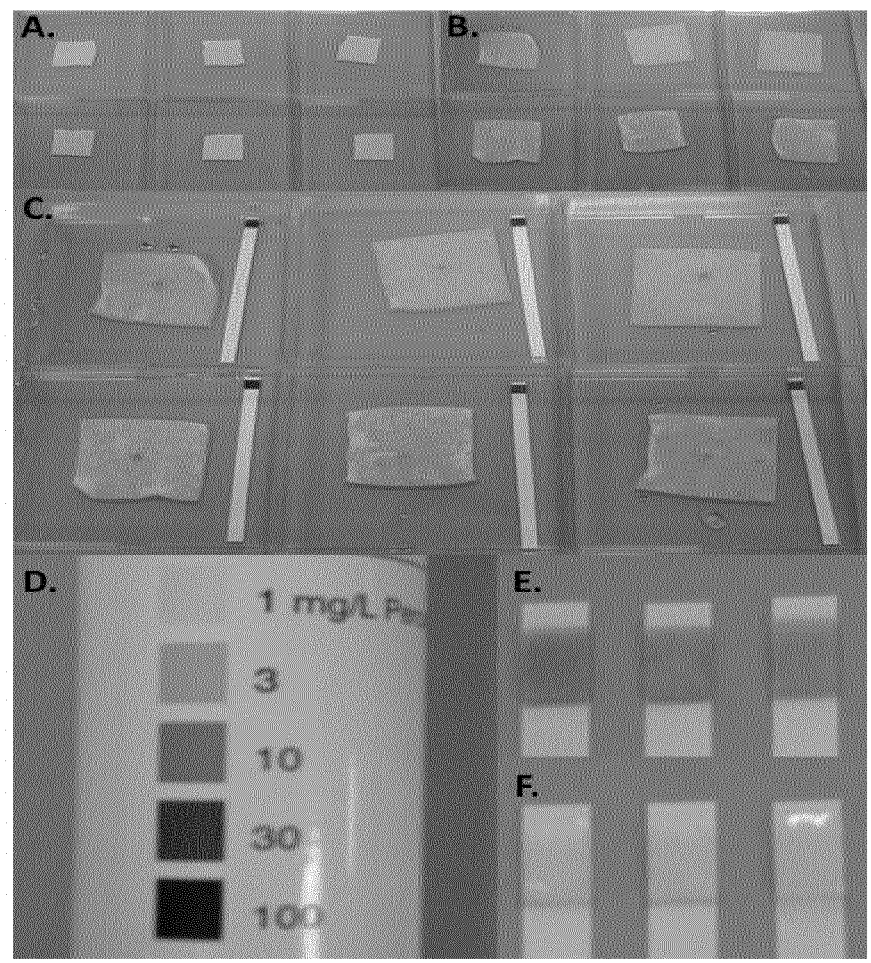

FIG. 3: Analysis of hydrogen peroxide generation by polyurethane foam test samples. A. Samples of invention (upper) and control (lower) before hydration. B. Invention sample (upper) and control (lower) samples following hydration. C. Initial assessment of hydrogen peroxide generation from invention sample (upper) and control (lower) immediately post hydration indicates that all samples are generating >100 mg/l hydrogen peroxide. D. Scale used to assess hydrogen peroxide levels. E. Test strip assessment of invention samples at the 60 minute time point showing generation of 3-10 mg/l of hydrogen peroxide. F. Test strip assessment of control samples at the 60 minute time point showing no hydrogen peroxide generation.

EXAMPLES

Example 1

Method

Three prototype polyurethane foams were generated: A foam only, B foam with 5% (w/w) honey and C foam with 5% honey and glucose oxidase (5 mg in 50 g foam mixture), as follows:

Mixing and spreading of the foam was conducted within a fume hood. Two pieces of casting paper were place onto the glass plate surface (or alternative hard perfectly flat surface) and the spreader bar was set to the desired height (typically ~2.00 mm) and place on casting papers. De-ionised water 16.03 g, Primal 5.97 g and methanol 3.0 g was mixed in a disposable beaker. This water phase was added to Hypol 25.0 g and mixed. The mix was then poured straight away between two pieces of casting paper and spread to desired thickness thickness. The foam was then left to cure for 2-5 minutes and was considered cured when it did not break to the touch. The foam was dried in a fan assisted incubator oven set to 65° C. for 20 minutes to drive off excess water.

To generate foam with 5% honey, 2.5 g honey was mixed with the de-ionised water, Primal and methanol.

To generate the foam capable of generating hydrogen peroxide, 100 µl glucose oxidase solution made from combining 100 µl glucose oxidase solution (dH$_2$O with 5 mg glucose oxidase) was mixed with 13.53 g de-ionised water, 2.5 g honey, Primal 5.97 g, and methanol 3.0 g in a disposable beaker. This water phase was added to Hypol 25.0 g, as described above. The water phase is added to the Hypol phase and mixed and the resulting mix was then treated as above (i.e. poured and spread to desired thickness thickness, cured and dried).

Testing the Foam

The foam prototypes (2×2 cm samples) were hydrated with 2 ml dH$_2$O and incubated for 2 minutes to allow fluid to be absorbed. Following incubation hydrogen peroxide test strips (Peroxide 1000, Quantofix®) were exposed to each sample for 15 seconds. Hydrogen peroxide test strips were compared against the Peroxide 1000 colour chart indicating the level of hydrogen peroxide present.

Results

Only the sample containing both enzyme and substrate (C) elicited a colour change in the hydrogen peroxide text strips (see FIG. 1). The colour change indicated hydrogen peroxide levels generated by prototype foam C to be approximately 1000 mg/l (see FIG. 2).

It was surprising that the enzyme was still active following the manufacturing process. It was also surprising that the enzyme was able to form a complex with the substrate and therefore metabolise the substrate, despite the enzyme and substrate being integrated within the structure of the foam.

Example 2

A further assessment was conducted on a test sample i.e. polyurethane foam containing honey and glucose oxidase incorporated during production (produced as described in Example 1) compared to a control polyurethane foam where no honey and glucose oxidase had been incorporated during production, but were applied to the surface of the foam.

Three samples were taken (3×3 cm squares) from each of the foams. These samples were initially hydrated; the invention with 3 ml $dH_2O$ only and the control with 3 ml of $dH_2O$ containing glucose oxidase and honey (enzyme and substrate amounts in accordance with the invention). Samples were allowed to hydrate over a 2 minute period. All samples were then assessed over a 60 minute period with the foams rinsed every 10 minutes (50 ml $dH_2O$ for 1 minute). Hydrogen peroxide levels were assessed initially following hydration and then every 10 minutes following each rinse using test strips (QUANTOFIX® Peroxide 100).

Results

The control and invention samples both successfully hydrated absorbing the 3 mls of fluid applied. Initial assessment of both samples indicated hydrogen peroxide generation at >100 mg/l (see FIG. 3C).

Repeated rinsing of the control samples resulted in hydrogen peroxide levels diminishing. Hydrogen peroxide levels were maintained for the first 20 minutes, however these were seen to drop at the 30 minute time point. By 60 minutes no hydrogen peroxide was generated (see FIG. 3F).

Hydrogen peroxide generation by the invention samples was significantly higher after 60 minute compared to control samples (see FIGS. 3E and 3F). Reduction in hydrogen peroxide levels generated by the invention samples was not observed until the 40-50 minute time points and by the 60 minute assessment the invention samples were still generating hydrogen peroxide at 3-10 mg/l (see FIG. 3E).

This assessment highlights the benefits of inclusion of substrate and enzyme relevant for hydrogen peroxide generation directly into the foam, as opposed to addition of these elements post-manufacturing. Inclusion within the structure did not hinder hydrogen peroxide generation and was shown to provide benefits with regard prolonged production despite exposure to high fluid levels.

The invention claimed is:

1. A polyurethane foam wound dressing, the foam integrally comprising an oxidoreductase enzyme and a substrate for the oxidoreductase enzyme, wherein the polyurethane foam has a swellability in water of 100% to 800%, and wherein the weight of the substrate for the oxidoreductase enzyme is 1% to 10% of the weight of the polyurethane foam wound dressing, and wherein the substrate for the oxidoreductase enzyme is provided as honey.

2. The foam wound dressing of claim 1, wherein
the oxidoreductase enzyme is glucose oxidase and the substrate is glucose, or
the oxidoreductase enzyme is fructose oxidase and the substrate is fructose.

3. The foam wound dressing of claim 1, wherein the foam has a density of at least 0.28 $g/cm^3$ and comprises at least 0.1 mg enzyme per gram of foam.

4. The foam wound dressing of claim 1, wherein the foam is produced by mixing a polyurethane polymer, water, an oxidoreductase enzyme and a substrate for the oxidoreductase enzyme to produce a resulting product; and drying the resulting product.

5. The foam wound dressing of claim 4, wherein a monohydric alcohol and/or a rubber is added when producing the foam.

6. The polyurethane foam wound dressing of claim 1, wherein the foam is produced by mixing an isocyanate-capped prepolymer, water, methanol and an aqueous acrylic polymer emulsion to form a mixture and drying the mixture at between 60° C. and 100° C. for at least 5 minutes.

7. A method of treating a wound comprising applying the polyurethane foam wound dressing of claim 1 to a wound site.

8. The foam wound dressing of claim 3, comprising 0.1 mg to 1 mg enzyme per gram of foam.

9. The foam wound dressing of claim 3, comprising 5% (w/w) of substrate.

* * * * *